United States Patent
Zhu

[19]

[11] Patent Number: 6,002,478
[45] Date of Patent: Dec. 14, 1999

[54] SYSTEM AND METHOD OF DETERMINING TRACE ELEMENTS IN HIGH VISCOSITY LIQUIDS, AND POWDERS, UTILIZING LASER-ABLATION

[75] Inventor: Jianzhong Zhu, Omaha, Nebr.

[73] Assignee: Transgenomic Inc., Omaha, Nebr.

[21] Appl. No.: 09/044,672

[22] Filed: Mar. 20, 1998

[51] Int. Cl.[6] .................................................. G01N 21/73
[52] U.S. Cl. ........................ 356/316; 356/36; 356/318; 250/288
[58] Field of Search ................................ 356/36, 38, 313, 356/315, 316, 318; 250/288

[56] References Cited

U.S. PATENT DOCUMENTS

| | | | |
|---|---|---|---|
| 3,981,585 | 9/1976 | Belcher et al. | 356/36 |
| 4,220,414 | 9/1980 | Barringer | 356/36 |
| 4,561,777 | 12/1985 | Radziemski et al. | 356/38 |
| 5,194,910 | 3/1993 | Kirkpatrick, Jr. et al. | 356/70 |
| 5,470,757 | 11/1995 | Gagnon et al. | 356/36 |
| 5,537,207 | 7/1996 | Carlhoff et al. | 356/317 |

*Primary Examiner*—F. L. Evans
*Attorney, Agent, or Firm*—James D. Welch

[57] ABSTRACT

Disclosed are a laser ablation system and method for determining the presence of trace elements in liquid samples such as oils, and/or in powder samples. A sample containing microporous membrane is utilized to prevent "splashing", "splattering" and/or "scattering" of liquid and/or powder sample when laser contained sample effectively "nebulizing" energy is applied. The present invention is typically used in combination with an inductively coupled plasma and a detector system, such as an Atomic Emission Spectrometer or Mass Spectrometer.

19 Claims, 1 Drawing Sheet

SYSTEM AND METHOD OF DETERMINING TRACE ELEMENTS IN HIGH VISCOSITY LIQUIDS, AND POWDERS, UTILIZING LASER-ABLATION

TECHNICAL FIELD

The present invention relates to systems and methods of determining the presence of trace elements in high viscosity liquid samples such as oils, and/or in powder samples. More particularly the present invention is a method which utilizes a system comprised of a sample containing microporous membrane and a laser ablation system, typically in combination with an inductively coupled plasma and a detector system, (such as an Atomic Emission Spectrometer or Mass Spectrometer).

BACKGROUND

Analysis of low viscosity liquid and/or powder samples to determine the presence of analytes, (eg. trace elements and/or contaminates etc.), present therein, is often accomplished by "nebulization", followed by injection of said nebulization products into a detector system which can be comprised of, for instance, an Inductively Coupled Plasma-Atomic Emission Spectrometer (ICP-AES) or an Inductively Coupled Plasma-Mass Spectrometer (ICP-MS) system. Nebulization of low viscosity liquid sample or solvated powder sample, for instance, can often be easily achieved by Pneumatic, Direct Injection and Ultrasonic etc. sample nebulizer systems. Said nebulizer systems generally produce numerous small diameter droplets of analyte containing liquid, (eg. solvent), which, typically after desolvation, are suitable for injection into an Inductively Couple Plasma (ICP). (Note that a patent to Zhu et al., U.S. Pat. No. 5,259,254 describes an Ultrasonic Nebulizer system and a patent to Wiederin, U.S. Pat. No. 5,212,365 describes a Direct Injection Micronebulizer System).

High viscosity liquid samples, however, often can not be directly subjected to nebulization because of their viscosity limited flow properties. As a result, known sample preparation methods such as Ashing, Acid Digestion and/or Organic Solvent Dilution are practiced to provide a sample which can be effectively nebulized by typical nebulizer systems, and entered to an ICP-AES and/or ICP-MS. It is well recognized, however, that said Ashing, Acid Digestion and/or Organic Solvent Dilution sample preparation approaches are tedious and time consuming and practice thereof often does not result in desired sample analysis sensitivity and accuracy. The ashing approach, for instance, (which utilizes an oven or microwave source to convert a sample to an ash), often results in vaporization of, poor recovery of, and poor detection of highly volatile elements, (eg. boron, vanadium, arsenic, sulfur and phospherous), and as mentioned, said procedure can be very time consuming. The acid digestion approach, (which involves digestion of a sample by an acid (eg. nitric), followed by mixture with a solvent), is also very tedious and time consuming. For emphasis, it is noted that a simple low viscosity liquid sample nebulization procedure might require one (1) minute or so to practice, while an acid digestion might require, relatively speaking, four (4) to eight (8) hours. As well, the Organic Solvent Dilution approach often leads to introduction of added volatile organic solvents into a subsequently utilized ICP, and said volatile organic solvents can cause plasma instability and low analyte detection sensitivity.

An alternative sample preparation approach, which can produce effectively "nebulized" sample products appropriate for entry to an ICP, involves Laser Ablation. (It is noted that the practice of Laser Ablation involves application of focused Laser contain energy onto a sample, and requires on the order of seconds to practice). It is known that Laser Ablation is very well suited to use with solid samples, however, when Laser contained energy is applied to liquids and/or powder samples, the result often includes "splattering", "splashing" and/or "scattering" effects, rather than, (or in addition to), the desired effective "nebulization" effects. To date said "splattering", "splashing" and/or "scattering" effects have made application of Laser Ablation to "nebulize" liquid and/or powder samples impractical. A system and method which would essentially eliminate said "splattering", "splashing" and/or "scattering" effects, and which would allow Laser contained energy to be applied to a liquid and/or powder sample with the primary result being production of effectively "nebulized" sample, would therefore be of great utility. The present invention provides such a system and method.

With the foregoing in mind a search of patents was conducted with the result being that very little was found. A patent to Carlhoff et al., U.S. Pat. No. 5,537,207, however, was identified, as was a patent to Kirkpatric et al., U.S. Pat. No. 5,194,910. The former patent describes use of Lasers to produce a plasma from which are emitted wavelengths that identify the carbon-black content in materials, while the later patent describes spectroscopic analysis of light transmitted through oil. No known prior art, however, describes or even remotely suggests the sequestering of liquid and/or powder samples in pores present in a microporous membrane prior to application of Laser contained energy thereto to ablate said combination liquid and/or powder sample and microporous membrane, with the result primarily being effective "nebulization" of said liquid and/or powder sample, without accompanying, undesirable "splattering", "splashing" and/or "scattering". The present invention teaches such a utility providing system and method.

DISCLOSURE OF THE INVENTION

In its most basic sense, the present invention is a system for analyzing a sample, which sample is presented in a present invention sample system. Said present invention sample system is comprised of at least one sample selection from the group consisting of: (liquid and powder), and further comprises a microporous membrane, in pores of which microporous membrane is caused to be present said liquid and/or powder sample.

Also in its most basic sense, the present invention is the method of preparing a liquid and/or powder sample for laser ablation mediated analysis, comprising the step of causing said liquid and/or powder sample to be present within pores of a microporous membrane, thereby forming a sample system, such that in use, when laser contained energy is caused to ablate at least a portion of said sample system, essentially "nebulized" sample is formed without "splashing", "splattering" and/or "scattering" of said sample occurring. Said method basically comprises bringing the microporous membrane and sample into contact in a manner such that said sample is caused to flow into said pores in said microporous membrane.

It is of primary importance to understand that a preferred present invention sample system is made from a microporous membrane such as teflon, plastic and/or paper, and preferably, though not necessarily, has a pore size in the range of between 0.01 and 100 microns, (with the range of 0.01–10.0 microns being preferred). Pore size criteria is based upon the requirement that liquid and or powder sample be present in said sample system in sufficiently small individually sequestered quantities so that when laser contained ablation energy is applied thereto significant "splashing", "splattering" and/or "scattering" of said sample liquid and/or powder sample does not occur.

The present invention system for analyzing a sample further comprises a laser ablation system for directing laser contained energy onto said sample system, and a means for containing said sample system while laser contained energy provided by said laser ablation system is directed onto said sample system thereby causing at least a portion of said sample system to become ablated. Said means for containing said sample system comprises a means for entering a flow of carrier gas, and an exit means for allowing carrier gas in which there has been caused to be present, by said ablation, effectively "nebulized" liquid and/or powder which was present in said sample system to exit through, and further comprises source of carrier gas and a detection system selected from the group consisting of: (an inductively coupled plasma-atomic emission spectrometer and an inductively coupled plasma-mass spectrometer). In use a flow of carrier gas from said source of carrier gas is caused to enter said means for entering carrier gas, and said laser ablation system is caused to apply laser contained energy to said sample system such that liquid and/or powder present in said sample system is caused to, by said ablation, be effectively "nebulized". Said effectively "nebulized" liquid and/or powder is caused to enter said carrier gas and exit via said exit means for allowing carrier gas in which there has been caused to be present, by said ablation, effectively "nebulized" liquid and/or powder which was present in said sample system to exit, and then enter said detection system selected from the group consisting of: (an inductively coupled plasma-atomic emission spectrometer and an inductively coupled plasma-mass spectrometer) for analysis therein.

The present invention system for analyzing a sample as typically embodied further comprises a laser reflection means, and a laser focusing means in said laser ablation system for directing laser contained energy onto said sample system with a spot size of between ten (10) microns and one (1) millimeter. In addition, a present invention system further typically comprises a sample system supporting stage in combination with a means to cause said stage to move, with said means to cause said stage to move preferably being a stepper motor which can effect one (1) micron step movements of said sample system supporting stage in at least one direction.

In use then, a flow of carrier gas from a source of carrier gas is caused to enter said means for entering carrier gas, and said laser ablation system is caused to apply laser contained energy to said sample system such that liquid and/or powder present in said sample system is caused to, by said ablation, be effectively "nebulized" and such that said effectively "nebulized" liquid and/or powder is caused to enter said carrier gas and exit said exit means for allowing carrier gas in which there has been caused to be present, by said ablation, effectively "nebulized" liquid and/or powder which was present in said sample system to exit, and then enter said detection system selected from the group consisting of: (an inductively coupled plasma-atomic emission spectrometer and an inductively coupled plasma-mass spectrometer) for analysis therein.

A method for analyzing a sample selected from the group consisting of: (a liquid and a powder), comprising the steps of:

a. providing a system for analyzing a sample comprising a sample system as described infra herein;

b. preparing a sample for laser ablation mediated analysis, comprising causing said sample which is comprised of at least one selection from the group consisting of: (liquid and powder), to be present within a pores of a microporous membrane, thereby forming a sample system, then placing said sample system on said sample system supporting stage;

c. causing said laser ablation system for directing laser contained energy onto said sample system to direct laser contained energy onto said sample system and thereby cause at least a portion of said sample system to become ablated;

d. causing a flow of carrier gas from said source of carrier gas to enter said means for entering carrier gas, and exit via said exit means for allowing carrier gas, in which there has been caused to be present, by said ablation, effectively "nebulized" liquid and/or powder which was present in said sample system to exit;

e. causing said flow of carrier gas exiting via said exit means for allowing carrier gas in which there has been caused to be present, by said ablation, effectively "nebulized" liquid and/or powder which was present in said sample system to exit, to enter said detection system selected from the group consisting of: (an inductively coupled plasma-atomic emission spectrometer and an inductively coupled plasma-mass spectrometer) for analysis therein.

Said method for analyzing a sample selected from the group consisting of: (a liquid and a powder), can further comprise the step of causing said means to cause a present sample system supporting stage to move, to move said sample system supporting stage during use.

It is noted that the described laser ablation causes ablated products which arise from the microporous membrane to enter the carrier gas. It is therefore present invention practice to utilize microporous membranes made of materials which do not interfere with ICP-AES or ICP-MS analysis of trace elements and/or contaminates in a sample, or to compensate for the presence of said microporous membrane material ablation products.

It is also noted that application of the ablating laser contained energy can be in the form of a short pulse, or can be applied over a period of time with said stage stationary or moving. In addition, signal measurement can involve integration over a period of time.

A primary focus of the present invention, it should then be appreciated, is provision of a system and method which allows laser ablation of liquid and/or powder samples, without accompanying "splashing", "splattering" and/or "scattering" of said sample occurring.

It is also noted that a present invention sample system allows convenient storage of secured sample, allows analysis of minimal amounts of sample and allows achieving better sensitivity than is possible utilizing conventional dilution, acid digestion and/or ashing techniques. Practice of the present invention typically allows achieving sensitivities of 0.02–1.0 PPM and 1.0–10.0 PPB where ICP-AES and ICP-MS systems, respectively, are utilized as detector.

The present invention will be better understood by reference to the Detailed Description Section of this Disclosure in conjunction with the accompanying Drawings.

SUMMARY OF THE INVENTION

It is therefore a primary purpose of the present invention to provide a system which enables laser ablation techniques to be applied to liquid and powder samples without causing adverse "splashing", "splattering" or "scattering".

It is another purpose of the present invention to teach the formation of a sample system comprised of a microporous membrane in the pores of which is caused to be present liquid and/or powder sample.

It is yet another purpose of the present invention to teach a sample system which allows convenient storage of liquid and/or powder sample.

It is another purpose yet of the present invention to teach a sample system which allows analysis liquid and/or powder samples utilizing minimal amounts thereof.

DETAILED DESCRIPTION

Figure 1:
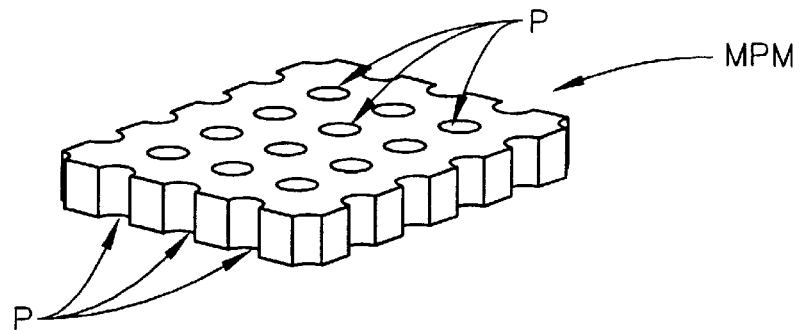
FIG. 1 demonstrates a microporous membrane with a multiplicity of pores present therein. Present invention practice provides that said pores be filled with liquid and/or powder sample and said resulting present invention sample system be subjected to laser ablation, in use.

Turning now to the Drawings, there is indicated in FIG. 1 a Microporous Membrane (MPM) with a multiplicity of Pores (P) present therein. In use, within present invention teachings, said Pores (P) are caused to be filled with liquid and/or powder sample to form a present invention Sample System (SS). As described in the Disclosure Of The Invention Section of this Disclosure, said present invention Sample System (SS) can then be subjected to laser ablation to provide essentially "nebulized" liquid and/or powder sample without accompanying "splashing", "splattering" and/or "scattering" of said sample occurring.

It is of primary importance to understand that a preferred present invention Sample System (SS) is made from a Microporous Membrane (MPM) such as Teflon (PTFE), Plastic and/or Paper etc., and preferably, though not necessarily, has a Pore (P) size in the range of between 0.01 and 100 microns, (with a range of 0.01 to 10.0 microns being most preferred). Pore (P) size determining criteria is based upon the requirement that liquid and or powder sample be present in said Sample System (SS) in sufficiently small individually sequestered quantities so that when laser contained ablation energy is applied thereto significant "splashing", "splattering" and/or "scattering" of said sample liquid and/or powder sample does not occur.

It is also noted that the described laser ablation causes ablated essentially "nebulized" products which arise from the Microporous Membrane (MPM) to enter a Carrier Gas and be transported to a Detector System (DET). (This will be understood by reference to FIG. 2.) It is therefore present invention practice to utilize Microporous Membranes (MPM) made of materials which do not interfere with, for instance, Inductively Coupled Plasma-Atomic Emission Spectrometer ICP-AES or Inductively Coupled Plasma-Mass Spectrometer ICP-MS analysis of trace elements and/or contaminates in a sample, or to compensate for the presence of said Microporous Membrane (MPM) material ablation products.

Figure 2:
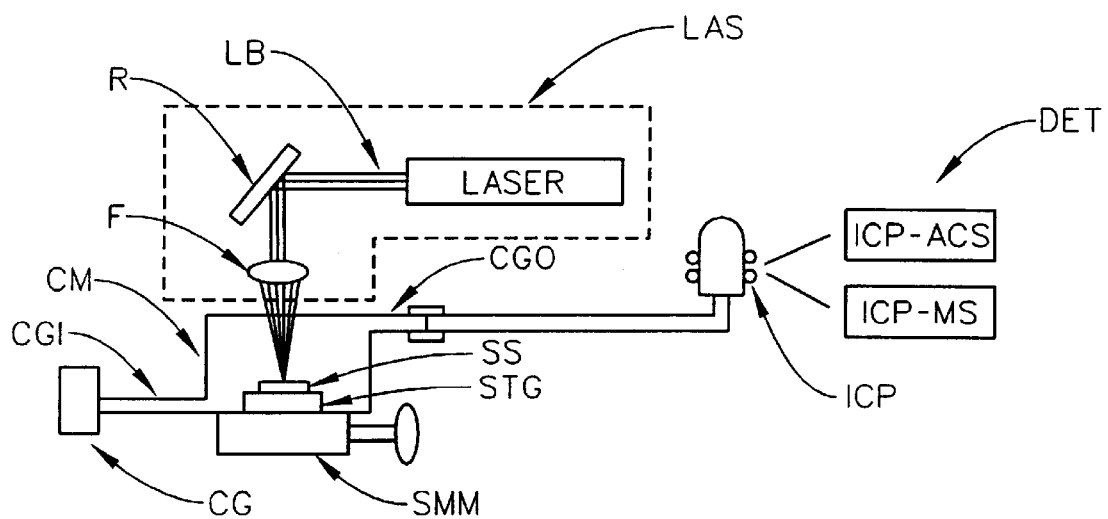
FIG. 2 shows a system appropriate for practice of the present invention method.

Turning now to FIG. 2 it will be appreciated that the present invention system for analyzing a sample further comprises a Laser Ablation System (LAS) for directing laser contained energy onto said Sample System (SS), and a Means for Containing (CM) said Sample System (SS) while laser contained energy provided by said Laser Ablation System (LAS) is directed onto said Sample System (SS) thereby causing at least a portion of said Sample System (SS) to become ablated. Said Means for Containing (CM) said Sample System (SS) comprises a means for entering a flow of Carrier Gas (CGI), and an Exit Means (CGO) for allowing carrier gas in which there has been caused to be present, by said ablation, effectively "nebulized" liquid and/or powder which was present in said sample system to exit through, and further comprises source (CG) of carrier gas and a Detection System (DET) typically selected from the group consisting of: (an Inductively Coupled Plasma-Atomic Emission Spectrometer ICP-AES and an Inductively Coupled Plasma-Mass Spectrometer ICP-MS). In use a flow of Carrier Gas from said Source (CG) of Carrier Gas is caused to enter said Means for entering Carrier Gas (CGI), and said Laser Ablation System (LAS) is caused to apply laser contained energy to said Sample System (SS) such that liquid and/or powder present in said Sample System (SS) is caused to, by said ablation, be effectively "nebulized". Said effectively "nebulized" liquid and/or powder is caused to enter said Carrier Gas and exit via said Exit Means (CGO) for allowing carrier gas in which there has been caused to be present, by said ablation, effectively "nebulized" liquid and/or powder which was present in said Sample System (SS) to exit, and then enter said Detection System (DET) typically selected from the group consisting of: (an Inductively Coupled Plasma-Atomic Emission Spectrometer ICP-AES and an Inductively Coupled Plasma-Mass Spectrometer ICP-MS) for analysis therein.

The present invention system for analyzing a sample as typically embodied further comprises a Laser Reflection Means (R), and a Laser Focusing Means (F) in said Laser Ablation System (LAS) for directing laser contained energy onto said Sample System (SS) with a spot size of between ten (10) microns and one (1) millimeter. In addition, a present invention system further typically comprises a Sample System (SS) Supporting Stage (STG) in combination with a Means To Cause Said Sample System (SS) Supporting Stage (STG) to move, with said means to cause said Means To Cause Said Sample System (SS) Supporting Stage (STG) to move preferably being a Stepper Motor (SMM) which can effect one (1) micron step movements of said sample system supporting stage in at least one (1) direction, and typically in two (2) directions.

In use then, a Flow of Carrier Gas from a Source (CG) of Carrier Gas is caused to enter said Means for Entering Carrier Gas (CGI), and said Laser Ablation System (LAS) is caused to apply laser contained energy to said Sample System (SS) such that liquid and/or powder present in said sample system is caused to, by said ablation, be effectively "nebulized" and such that said effectively "nebulized" liquid and/or powder is caused to enter said Carrier Gas and exit said Exit Means (CGO) for allowing Carrier Gas in which there has been caused to be present, by said ablation, effectively "nebulized" liquid and/or powder which was present in said sample system to exit, and then enter said detection system typically selected from the group consisting of: (an Inductively Coupled Plasma-Atomic Emission Spectrometer ICP-AES and an Inductively Coupled Plasma-Mass Spectrometer ICP-MS) for analysis therein.

Figure 3:
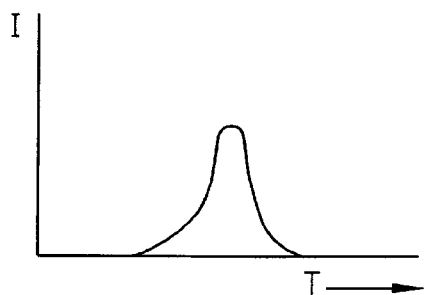
FIG. 3 shows a typical pulsed laser ablation detector signal achievable utilizing the present invention, where a liquid and/or powder sample in a microporous membrane is investigated.
Figure 4:
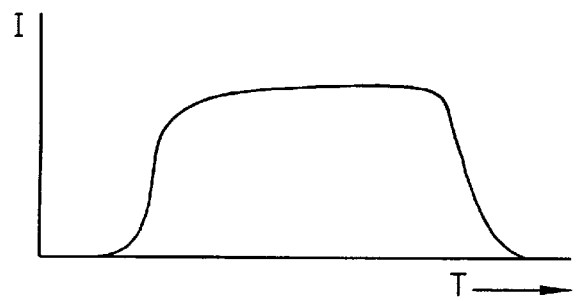
FIG. 4 shows a typical prolonged laser ablation detector signal achievable utilizing the present invention, where a liquid and/or powder sample in a microporous membrane is investigated.

As demonstrated by the Detector Signal Plot in FIG. 3, it is noted that application of the ablating laser contained energy can be in the form of a short pulse, or, as demonstrated by the Detector Signal Plot in FIG. 4, can be applied over a period of time with said Sample System (SS) Supporting Stage (STG) held stationary or moving. In addition, signal measurement can involve integration over a period of time. For reference, it is noted that where a ICP-AES system is utilized as Detector (DET) that sensitivity in the range of 0.02 to 1.0 PPM can be achieved utilizing the present invention, and that where a ICP-MS system is utilized as Detector (DET) that sensitivity in the range of 1.0 to 10.0 PPB can be achieved utilizing the present invention.

A primary focus of the present invention, it should then be appreciated, is provision of a system and method which allows laser ablation of liquid and/or powder samples, without accompanying "splashing", "splattering" and/or "scattering" of said sample occurring.

Having hereby disclosed the subject matter of the present invention, it should be apparent that many modifications, substitutions, and variations of the present invention are possible in light thereof. It is to be understood that the present invention can be practiced other than as specifically described and should be limited in scope and breadth only by the appended claims.

I claim:

1. A sample system which enables storage, and laser ablation without "splashing", "splattering" or "scattering" of a sample selected from the group consisting of:
   liquid and powder;
   said sample system being comprised of at least one selection from the group consisting of:
   liquid and powder;
   in functional combination with a microporous membrane which is comprised of a multiplicity of pores;
      said liquid and/or powder sample being substantially uniformly present in said multiplicity of pores of said microporous membrane;
      the improvement being that said pores in said microporous membrane which substantially uniformly contain said liquid and/or powder sample are of a size such that contained liquid and/or powder sample is present in said sample system in an amount which does not "splash", "splatter" or "scatter" when said sample system is ablated by application of laser energy as does said liquid and/or powder sample when ablated by direct application thereto of identical laser energy.

2. A system for analyzing a sample as in claim 1, in which said microporous membrane is made of a material with a pore size of between 0.01 and 100 microns.

3. A system for analyzing a sample as in claim 1 in which the microporous membrane is made of a material selected from the group consisting of:
   teflon, plastic and paper.

4. A system for analyzing a sample as in claim 1 which further comprises a laser ablation system for directing laser contained energy onto said sample system.

5. A system for analyzing a sample as in claim 4, which further comprises a means for containing said sample system while laser contained energy provided by said laser ablation system is directed onto said sample system thereby causing at least a portion of said sample system to become ablated, said means for containing said sample system comprising a means for entering a flow of carrier gas, and an exit means for allowing carrier gas, in which there has been caused to be present, by said ablation, effectively "nebulized" liquid and/or powder which was present in said sample system, to exit.

6. A system for analyzing a sample as in claim 5, which further comprises a source of carrier gas and a detection system selected from the group consisting of:
   an inductively coupled plasma-atomic emission spectrometer and an inductively coupled plasma-mass spectrometer;
   such that in use a flow of carrier gas from said source of carrier gas is caused to enter said means for entering carrier gas, and such that said laser ablation system is caused to apply laser contained energy to said sample system such that liquid and/or powder present in said sample system is caused to, by said ablation, be effectively "nebulized" and such that said effectively "nebulized" liquid and/or powder is caused to enter said carrier gas and exit via said exit means for allowing carrier gas, in which there has been caused to be present, by said ablation, effectively "nebulized" liquid and/or powder which was present in said sample system, to exit, and then enter said detection system selected from the group consisting of:
   an inductively coupled plasma-atomic emission spectrometer and an inductively coupled plasma-mass spectrometer for analysis therein.

7. A system for analyzing a sample as in claim 4, which further comprises a at least one member of the group consisting of:
   a laser reflection means, and a laser focusing means in said laser ablation system for directing laser contained energy onto said sample system with a spot size of between ten (10) microns and one (1) millimeter.

8. A system for analyzing a sample in claim 4, which further comprises a sample system supporting stage in combination with a means to cause said stage to move.

9. A system for analyzing a sample as in claim 8, in which said means to cause said sample system supporting stage to move comprises a stepper motor.

10. A system for analyzing a sample as in claim 9, in which said stepper motor can effect one (1) micron step movements of said sample system supporting stage in at least one direction.

11. A sample system which enables storage, and laser ablation without "splashing", "splattering" or "scattering" of a sample selected from the group consisting of:
   liquid and powder;
   as in claim 1, in which the sample is selected to be analyte containing oil.

12. A method of preparing a sample selected from the group consisting of:
   liquid and powder;
   for a purpose selected from the group consisting of:
   storage, and laser ablation mediated analysis;
   comprising the steps of:
   a. selecting a microporous membrane with a pore size such that when said pores are caused to substantially uniformly contain said liquid and/or powder sample thereby forming a sample system, said contained liquid and/or powder sample is present in an amount in said sample system which does not "splash", "splatter" or "scatter" when said sample system is ablated by application of laser energy as does said liquid and/or powder sample when ablated by direct application thereto of identical laser energy; and
   b. causing said sample to be present substantially uniformly within said pores of said selected microporous membrane; and c. optionally applying laser contained energy to ablate at least a portion of said sample system, such that essentially "nebulized" sample is formed without "splashing", "splattering" or "scattering" of said sample occurring as occurs when said liquid and/or powder sample is ablated by direct application thereto of identical laser energy.

13. A system for analyzing a sample comprising a sample system, said sample system being comprised of at least one sample selected from the group consisting of:

liquid and powder;

in functional combination with a microporous membrane with pore size in the range of 0.01 to 100 microns, in said pores there being substantially uniformly present said liquid and/or powder sample; said microporous membrane being made of at least one material selected from the group consisting of:

teflon, plastic and paper;

which system for analyzing a sample further comprises a laser ablation system for directing laser contained energy onto said sample system and a means for containing said sample system while laser contained energy provided by said laser ablation system is directed onto said sample system thereby causing at least a portion of said sample system to become ablated, said means for containing said sample system comprising a means for entering a flow of carrier gas, and an exit means for allowing carrier gas, in which there has been caused to be present, by said ablation, effectively "nebulized" liquid and/or powder sample which was present in said sample system, to exit; which system for analyzing a sample further comprises source of carrier gas and a detection system selected from the group consisting of:

an inductively coupled plasma-atomic emission spectrometer and an inductively coupled plasma-mass spectrometer;

such that in use a flow of carrier gas from said source of carrier gas is caused to enter said means for entering carrier gas, and such that said laser ablation system is caused to apply laser contained energy to said sample system such that liquid and/or powder sample present in said sample system is caused to, by said ablation, be effectively "nebulized" and such that said effectively "nebulized" liquid and/or powder sample is caused to enter said carrier gas and exit said exit means for allowing carrier gas in which there has been caused to be present, by said ablation, effectively "nebulized" liquid and/or powder sample which was present in said sample system to exit, and then enter said detection system selected from the group consisting of:

an inductively coupled plasma-atomic emission spectrometer and an inductively coupled plasma-mass spectrometer for analysis therein;

the improvement being that said pores in said microporous membrane which substantially uniformly contain said liquid and/or powder sample are of a size such that contained liquid and/or powder sample is present in said sample system in an amount which does not "splash", "splatter" or "scatter" when said sample system is ablated by application of laser energy as does said liquid and/or powder sample when ablated by direct application thereto of identical laser energy.

14. A system for analyzing a sample as in claims 13, which further comprises a at least one member of the group consisting of:

a laser reflection means, and a laser focusing means in said laser ablation system for directing laser contained energy onto said sample system with a spot size of between ten (10) microns and one (1) millimeter.

15. A system for analyzing a sample as in claim 13, which further comprises a sample system supporting stage in combination with a means to cause said stage to move.

16. A system for analyzing a sample as in claim 15, in which said means to cause said sample system supporting stage to move comprises a stepper motor.

17. A system for analyzing a sample as in claim 16, in which said stepper motor can effect one (1) micron step movements of said sample system supporting stage in at least one direction.

18. A method for analyzing a sample selected from the group consisting of:

a liquid and a powder;

comprising the steps of:

a. providing a system for analyzing a sample comprising a sample system, said sample system being comprised of at least one selection from the group consisting of: liquid and powder;

said sample system further comprising a microporous membrane in which is substantially uniformly present said liquid and/or powder sample; said microporous membrane being made of at least one material selected from the group consisting of:

teflon, plastic and paper with a pore size of between 0.01 and 100 microns; which system for analyzing a sample further comprises a sample system supporting stage in combination with a means to cause said stage to move; which system for analyzing a sample further comprises a laser ablation system for directing laser contained energy onto said sample system while supported upon said sample system supporting stage, and a means for containing said sample system while laser contained energy provided by said laser ablation system is directed onto said sample system to the end that at least a portion of said sample system becomes ablated; said means for containing said sample system comprising a means for entering a flow of carrier gas, and an exit means for allowing carrier gas, in which there has been caused to be present, by said ablation, effectively "nebulized" liquid and/or powder which was present in said sample system, to exit; which system for analyzing a sample further comprises source of carrier gas and a detection system selected from the group consisting of:

an inductively coupled plasma-atomic emission spectrometer and an inductively coupled plasma-mass spectrometer;

such that in use a flow of carrier gas from said source of carrier gas can be caused to enter said means for entering carrier gas, and such that said laser ablation system can be caused to apply laser contained energy to said sample system such that liquid and/or powder present in said sample system is caused to, by said ablation, be effectively "nebulized" and such that said effectively "nebulized" liquid and/or powder is caused to enter said carrier gas and exit said exit means for allowing carrier gas in which there has been caused to be present, by said ablation, effectively "nebulized" liquid and/or powder which was present in said sample system to exit, and then enter said detection system selected from the group consisting of:

an inductively coupled plasma-atomic emission spectrometer and an inductively coupled plasma-mass spectrometer for analysis therein;

the improvement being that said pores in said microporous membrane which substantially uniformly contain said liquid and/or powder sample are of a size such that contained liquid and/or powder sample is present in said sample system in an amount which does not “splash”, “splatter” or “scatter” when said sample system is ablated by application thereto of laser energy as does said liquid and/or powder sample when ablated by direct application of identical laser energy;

b. placing, on said sample system supporting stage, a sample system comprised of at least one selection from the group consisting of:
liquid and powder;

said sample system further comprising a microporous membrane in which is present said liquid and/or powder sample in an amount which does not “splash”, “splatter” or “scatter” when said sample system is ablated by application of laser energy as does said liquid and/or powder sample when ablated by direct application of identical laser energy;

c. causing said laser ablation system for directing laser contained energy onto said sample system to direct laser contained energy onto said sample system and thereby cause at least a portion of said sample system to become ablated without said liquid and/or powder sample “splashing”, “splattering” or “scattering” as does said liquid and/or powder sample when ablated by direct application thereto of identical laser energy;

d. causing a flow of carrier gas from said source of carrier gas to enter said means for entering carrier gas, and exit via said exit means for allowing carrier gas, in which there has been caused to be present, by said ablation, effectively “nebulized” liquid and/or powder which was present in said sample system to exit;

e. causing said flow of carrier gas exiting via said exit means for allowing carrier gas in which there has been caused to be present, by said ablation, effectively “nebulized” liquid and/or powder which was present in said sample system to exit, to enter said detection system selected from the group consisting of:

an inductively coupled plasma-atomic emission spectrometer and an inductively coupled plasma-mass spectrometer for analysis therein.

19. A method for analyzing a sample selected from the group consisting of:

a liquid and a powder;

as in claim 18 which further comprises the step of causing said means to cause said sample system supporting stage to move, to move said sample system supporting stage during use.

* * * * *